(12) United States Patent
McGann (10) Patent No.: US 6,786,719 B2
(45) Date of Patent: Sep. 7, 2004

(54) ORTHODONTIC BRACKET HOLDER

(75) Inventor: Benson McGann, San Juan Capistrano, CA (US)

(73) Assignee: Progressive America, Inc., Santa Ana, CA (US)

( * ) Notice: Subject to any disclaimer, the term of this patent is extended or adjusted under 35 U.S.C. 154(b) by 0 days.

(21) Appl. No.: 10/187,494

(22) Filed: Jul. 1, 2002

(65) Prior Publication Data

US 2003/0134250 A1 Jul. 17, 2003

Related U.S. Application Data

(60) Provisional application No. 60/350,232, filed on Jan. 16, 2002.

(51) Int. Cl.[7] .................................................. A61C 3/00
(52) U.S. Cl. ............................................ 433/4; 433/72
(58) Field of Search ............................. 433/3, 4, 72, 75

(56) References Cited

U.S. PATENT DOCUMENTS

| | | | |
|---|---|---|---|
| 3,686,762 A | * 8/1972 | Sutter | 433/4 |
| 4,850,864 A | 7/1989 | Diamond | 433/3 |
| 5,304,061 A | 4/1994 | Nelson | 433/8 |
| 5,312,248 A | 5/1994 | Zandkarimi | 433/3 |
| 5,810,582 A | 9/1998 | Doyle | 433/4 |
| 5,868,787 A | 2/1999 | Kim | 606/211 |
| 6,296,482 B1 | 10/2001 | Kapit | 433/3 |
| 6,334,772 B1 | * 1/2002 | Taub et al. | 433/24 |
| 6,447,291 B2 | * 9/2002 | Kim | 433/4 |

OTHER PUBLICATIONS http://www.sankin-dental.co.jp/english/kyosei/plier/bond1.html.

* cited by examiner

*Primary Examiner*—Todd E. Manahan
(74) *Attorney, Agent, or Firm*—Rutan & Tucker (57) ABSTRACT

An apparatus that includes a handle; a pair of opposed gripping members, each member comprising a gripping surface, each gripping surface comprising a forward edge; and a gripping member position and orientation indicator (GMPOI) positioned between the handle and the forward edges. A method of coupling an orthodontic bracket to a tooth comprising: providing a bracket holder comprising a gripping member position and orientation indicator (GMPOI); utilizing the bracket holder to grip a bracket and to place the bracket on a tooth; while viewing the position and orientation of the GMPOI relative to the tooth on which the bracket is being mounted, rotating and/or moving the bracket holder so as to set the orientation and position of the bracket; subsequently causing the bracket holder to release the bracket; inserting a portion of the bracket holder into the bracket; and rotating the bracket holder so as to rotate the bracket.

14 Claims, 5 Drawing Sheets

ORTHODONTIC BRACKET HOLDER

This application claims the benefit of U.S. provisional application No. 60/350,232 filed Jan. 16, 2002 incorporated herein by reference in its entirety.

FIELD OF THE INVENTION

The field of the invention is tools with the preferred embodiments being particularly adapted for use in the field of orthodontic bracket placement, positioning, and alignment tools.

BACKGROUND OF THE INVENTION

Figure 1:
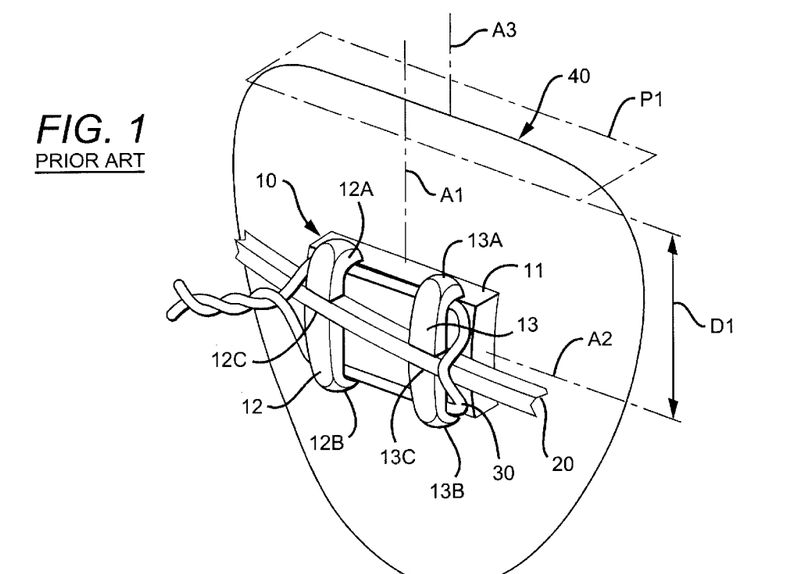
FIG. 1 is a perspective view of a bracket, archwire, and tooth assembly.

Dentists, orthodontists in particular, often use orthodontic hardware such as brackets and archwires in the prevention or correction of irregularities of the teeth. An orthodontic bracket is generally a metal or ceramic part fastened to a tooth to serve as a means for fastening an archwire. An archwire is a metal wire that is attached to the brackets to move the teeth of a patient in a manner desired by the patient's dentist. An example of a bracket and archwire assembly is shown in FIG. 1 with bracket 10 being bonded to tooth 40, and archwire 20 being coupled to bracket 10 by ligature wire 30. Bracket 10 comprises base 11, and stems 12 and 13. Stems 12 and 13 each comprise two tie wings (12A, 12B, 13A, and 13B) and an archwire receiving slot (12C and 13C). In FIG. 1, bracket 10 can be characterized as having perpendicular axis A1 and A2, and tooth 40 can be characterized as having a central axis A3, and an occlusal plane P1 as shown.

Figures 2A, 2B, 2C:
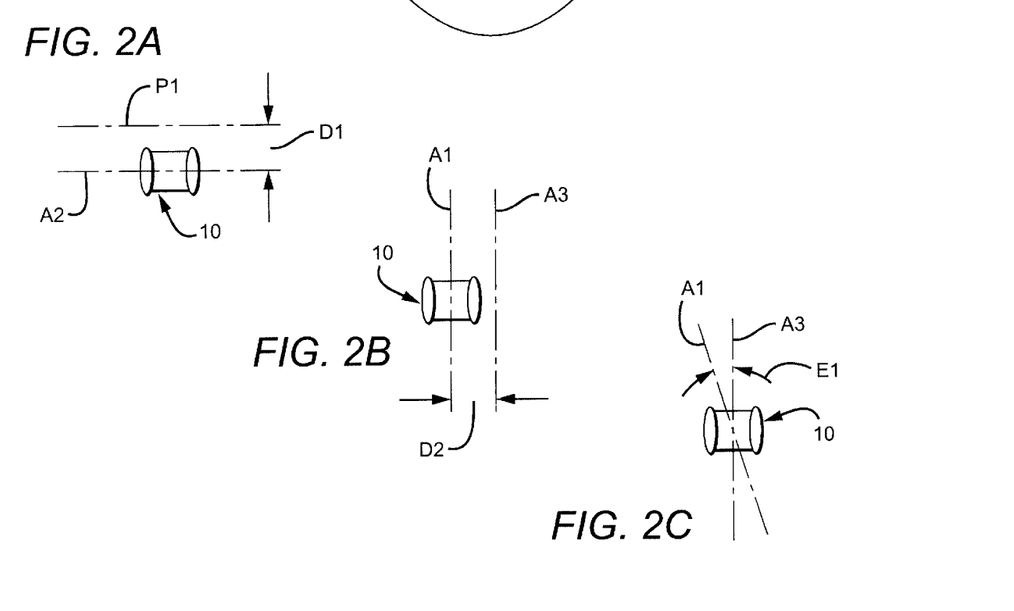
FIG. 2A is a schematic illustrating horizontal positioning of the bracket of FIG. 1 relative to the tooth of FIG. 1.
FIG. 2B is a schematic illustrating vertical positioning of the bracket of FIG. 1 relative to the tooth of FIG. 1.
FIG. 2C is a schematic illustrating orientation of the bracket of FIG. 1 relative to the tooth of FIG. 1.

Due to the small size of the brackets, it is generally desirable to use a holder such as a tweezers or pliers to pick up position bracket 10 on a tooth 40. The positioning and alignment of bracket 10 relative to tooth 40 is particularly important to a dentist, as it tends to strongly impact the movement of tooth 40 during treatment. As such, it is generally desirable to position bracket 10 at a particular height relative to the top/occlusal surface of the tooth. Referring to FIGS. 2A–2C, the position of bracket 10 may be adjusted such that: (a) the vertical distance D1, the distance between the occlusal plane P1 or occlusal surface of tooth 40 and horizontal axis A2, is a desired value; (b) the horizontal distance D2, the horizontal component of the distance between axis A1 of bracket 10 and axis A3 of tooth 40, is a desired value (possibly zero); and the angle E1 between axis A1 and axis A3 is a desired value (also possibly zero). Unfortunately, properly positioning and aligning bracket 10 is not always easy to accomplish. Because of this, tools for aiding in the holding, positioning, and aligning of brackets have been developed. Examples of such tools can be found at least in U.S. Pat. Nos. 5,868,787 and 4,850,864, in U.S. Pat. No. 5,810,582 and in U.S. Pat. Nos. 6,296,482, 5,312,248, and 5,304,061. However, this list is not exhaustive as other types of holders, gauges, and other tools are also known.

Figure 3:
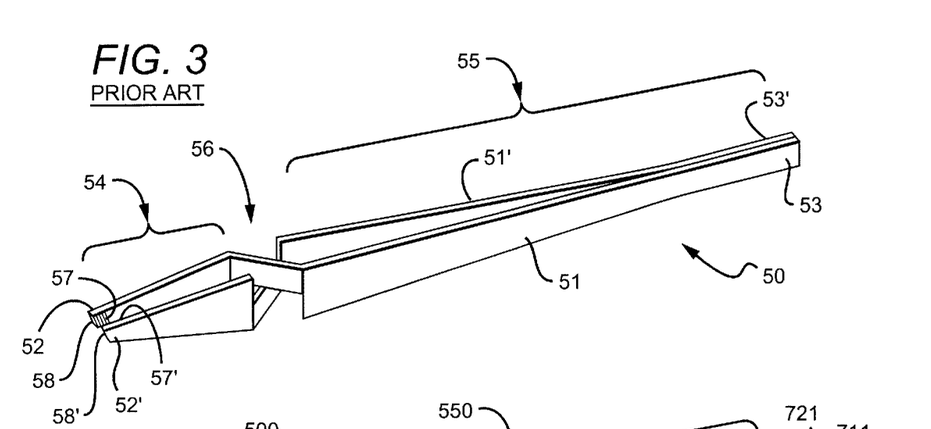
FIG. 3 is a perspective view of a prior art bracket holding tweezer.

One type of holder that is particularly suitable for comparison purposes is the bracket holding tweezer of FIG. 3. In FIG. 3, tweezer 50 comprises a pair of elongated members 51 and 51' placed in an adjacent lengthwise relationship with one another, each member having a first end part 52 and 52' and a second end part 53 and 53', the first end part forming a gripping mechanism 54, and the second end parts coupled together to form a handle 55. The tweezers of FIG. 3 is a pre-tensioned or cross-over type having a gripping mechanism 54 comprising a jaw which is held in the closed position by tension formed by the shape of the tweezers, in particular by the cross-over portion 56 and the coupling together of ends 53 and 53'. The user must apply pressure to the members 51 and 51' to open the jaw, align the object upon which the tweezers are to be used with, and then reduce the pressure on the members so that the object is held by the gripping area. In many instances, cross-over type holders are preferred in the placement of brackets on teeth.

The gripping jaw 54 that includes the first end parts 52 and 52' of the members 51 and 51', includes gripping surfaces 57 and 57' having front edges 58 and 58' that are typically used to grip the tie wings of an orthodontic bracket. The front edges 58 and 58' of the gripping jaws are typically inclined relative to a vertical axis to allow the holder to be angled away from the surface of a tooth during placement of a bracket. In some instances their front edges are cutting surfaces.

SUMMARY OF THE INVENTION

The present invention is directed to apparatus for holding, positioning, and aligning other apparatus such as orthodontic brackets. Preferred embodiments of such apparatus include one or more of the following: (a) a bracket gripping mechanism; (b) a horizontal position indicator; (c) a vertical position indicator; and (d) an orientation indicator. In preferred embodiments, various portions of the apparatus serve multiple purposes, and interact with other portions to facilitate use of the apparatus. A most preferred apparatus comprises a handle, a bracket gripping mechanism, a combined orientation and horizontal position indicator, and a height gauge (vertical position indicator) that can also cooperate with the handle as an orientation indicator.

It is advantageous for a given apparatus to comprise an indicator that extends vertically upward and/or downward from the apparatus with the indicator providing a visual representation of the location of a centerline of a bracket or other apparatus being positioned. It is also advantageous to have such an indicator be non-perpendicular to a handle portion of the apparatus. If an apparatus comprises jaws, it is advantageous to position a vertically extending indicator between the jaws such that the indicator is positioned at or near the center of the gap between the jaws when the jaws are being used to hold a bracket or other apparatus. If an apparatus comprises a holder having angled jaws, it is advantageous to have such a vertically extending indicator be parallel to the jaws so as to provide a visual indication of the orientation of the jaws. Any vertically extending indicator is preferred to be near an end of a given apparatus to allow it to be close to a bracket or other apparatus being positioned and orientated. However, in the case of an orthodontic bracket holder, it is preferred that such vertically extending indicator be set at least slightly back from an end of the holder so as to avoid contact with the teeth and gums of a patient during use.

It is advantageous to be able to use most of the length of an elongated apparatus to provide a visual indication of the orientation of a bracket or other apparatus being positioned as the longer the indicator means is, the easier it is to determine improper orientation of the apparatus being positioned.

It is advantageous to include both position and orientation indicators on a holder apparatus so as to allow a bracket or other apparatus to be positioned and aligned without having to utilize a separate tool. It is contemplated that one advantage of using such an apparatus is that, particularly when dealing with using a fast setting bonding material to bond a bracket to a tooth, proper position and orientation can be obtained earlier during the setting process with a resultant reduction in risk of damage to the bond that that can be caused by movement during later stages of the setting process.

A desirable apparatus can be obtained by modifying an existing bracket holder by adding a height gauge to the handle of a standard bracket holder, and mounting a vertical bar near the jaws of the holder. In such a configuration, the vertical bar can be used simultaneously as both a position and orientation indicator. The height gauge can be used first as a height gauge, and subsequently as an orientation indicator in cooperation with a handle of the holder.

It is preferred that an included height gauge have a bracket contact portion set at a fixed distance from a tooth contacting portion will be advantageous. It is also preferred that the bracket contact portion be adapted to fit within the archwire receiving slots of the stems of a bracket, and, preferably, to comprise a wire loop or other mechanism that permits the bracket holder to be positioned horizontally while being received by the archwire receiving slots even if such slots are tilted upward or downward.

When a height gauge is part of a bracket holder, rotating the height gauge ninety degrees relative to the jaws of the holder will, in many instances, position the holder relative to the gauge so as to best cooperate with the gauge to act as an orientation indicator.

If a bracket holder apparatus comprises multiple planar members adapted to be partially inserted into a bracket or other apparatus, it is preferred that the members be co-planar and positioned relative to the remainder of the apparatus so as to best use the remainder of the apparatus of the orientation of the planar members.

It is contemplated that it is advantageous to provide orthodontic bracket holders in sets with each holder in the set being dedicated to positioning a bracket on a particular tooth, and each holder having a height gauge set to a fixed height that corresponds to the height at which a bracket is to be positioned on the tooth corresponding to the holder.

Various objects, features, aspects and advantages of the present invention will become more apparent from the following detailed description of preferred embodiments of the invention, along with the accompanying drawings in which like numerals represent like components.

DETAILED DESCRIPTION

Figure 4:
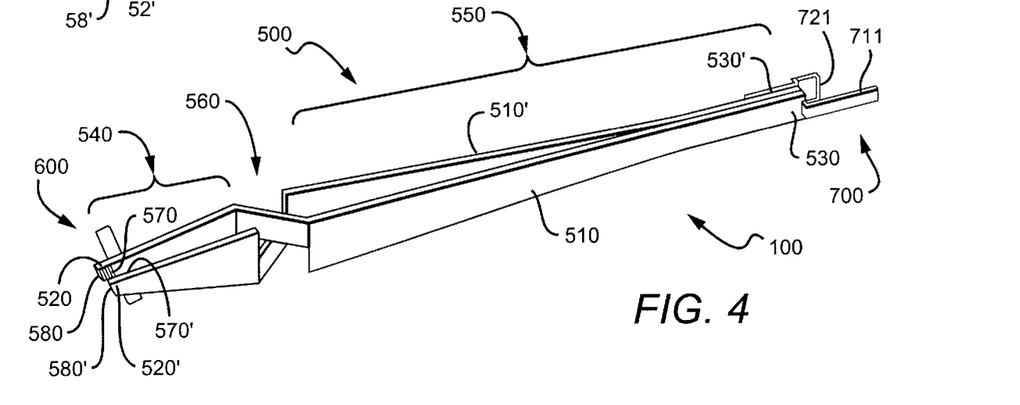
FIG. 4 is a perspective view of a preferred apparatus embodying the invention.
Figure 4A:
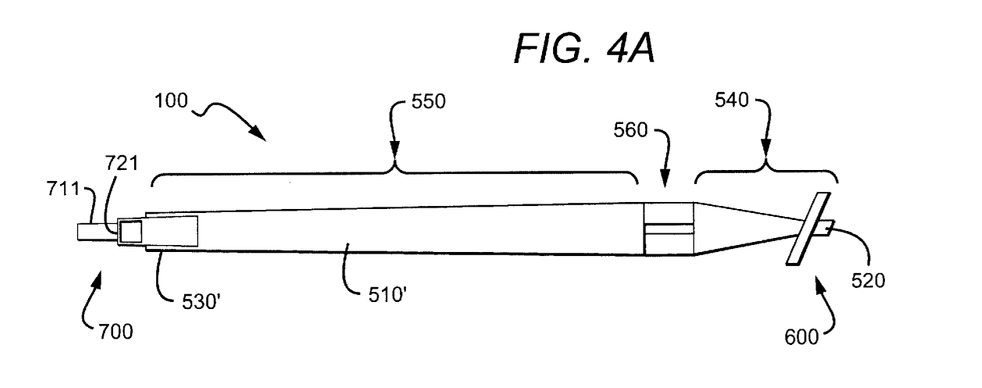
FIG. 4A is a side view of the apparatus of FIG. 4.
Figure 4B:
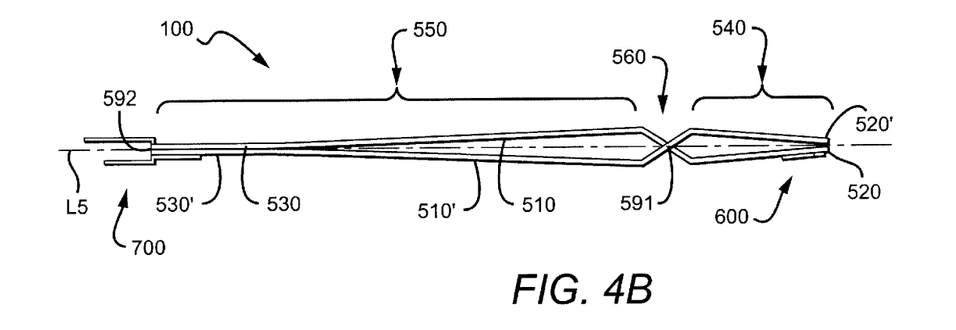
FIG. 4B is a top view of the apparatus of FIG. 4.
Figure 4C:
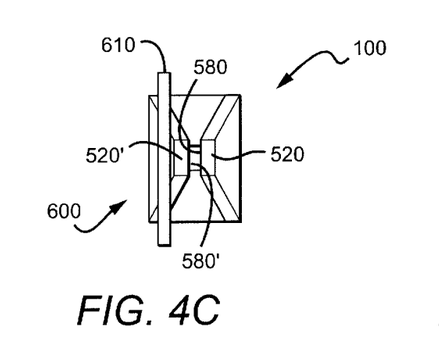
FIG. 4C is a front view of the apparatus of FIG. 4.
Figure 4D:
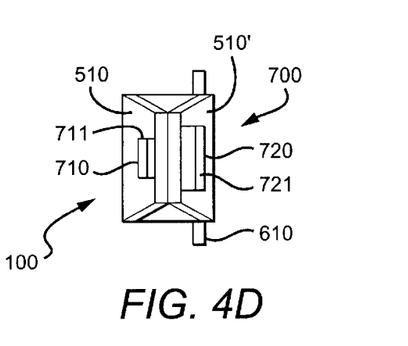
FIG. 4D is a back view of the apparatus of FIG. 4.
Figure 4E:
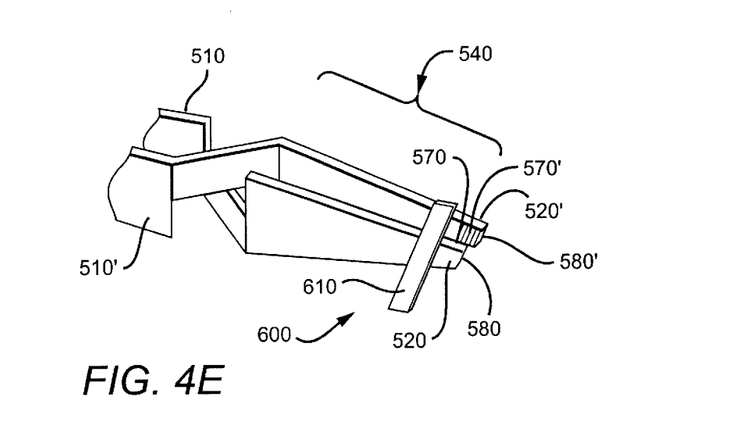
FIG. 4E is a detail view of the gripping mechanism portion of the apparatus of FIG. 4.

In FIG. 4, a preferred holder, positioning, and alignment apparatus 100 comprises a bracket holder 500, bracket/gripping member position and orientation indicator (hereinafter GMPOI) 600, and a bracket vertical position indicator/height gauge 700. Both GMPOI 600 and gauge 700 serve dual purposes as each can be used to both position and orient a bracket.

Figure 4F:
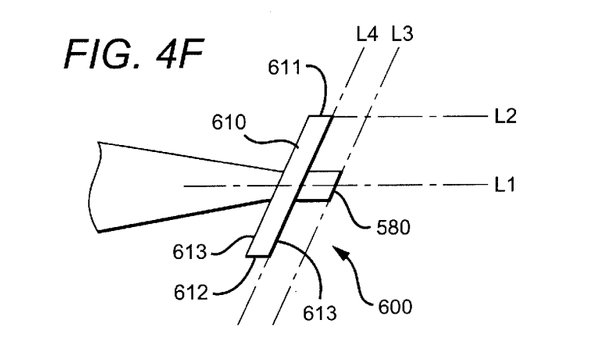
FIG. 4F is a detail view of a vertical indicator portion of the apparatus of FIG. 4.
Figure 4G:
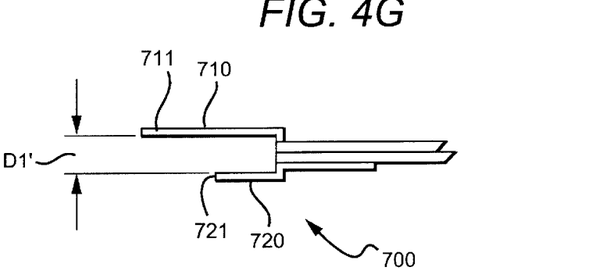
FIG. 4G is a detail view of a height indicator portion of the apparatus of FIG. 4.
Figure 4H:
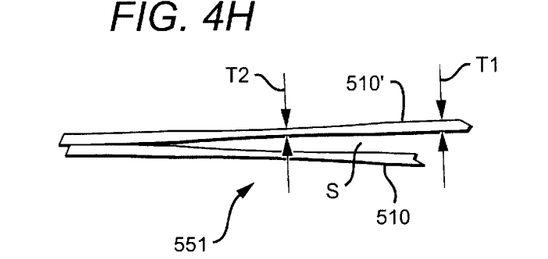
FIG. 4H is a detail view of a holder de-biasing portion of the apparatus of FIG. 4.

Referring to FIGS. 4A–4H, holder 500 comprises a pair of elongated members 510 and 510' placed in an adjacent lengthwise relationship with one another, each member having a first end part 520 and 520' and a second end part 530 and 530', the first end part forming a gripping mechanism 540, and the second end parts coupled together to form a handle 550. As with the tweezers of FIG. 3, the holder 500 is a pre-tensioned or cross-over type having a gripping mechanism 540 comprising a jaw which is held in the closed position by tension formed by the shape of the tweezers, in particular by the cross-over portion 560. The gripping jaw 540 includes the first end parts 520 and 520' of the members 510 and 510', includes gripping surfaces 570 and 570' having front edges 580 and 580' that are adapted for and used to grip the tie wings of an orthodontic bracket. The front edges 580 and 580' of the gripping jaws are inclined relative to a line L1 passing through the length of holder 500. In a preferred embodiment, a de-biasing portion 551 of either or both of members 510 and 510' is thinner than the remainder of the member so as to decrease the amount of force required to separate gripping surfaces 570 and 570'. In FIG. 4H thickness T2 is less than thickness T1, the thickness of a majority of member 510'. Holder 500 is preferably formed from elongated planar pieces of stainless steel.

It should be noted that the actual structure of holder 500 is not limited to that shown. Other contemplated embodiments of holder 500 will differ from the shown embodiment in regard to the materials used, form, and/or principle of operation. As would be obvious to one of average skill in the art, the methods and the position and orientation indicators disclosed herein are suitable for use with a large variety of holders.

Gripping member position and orientation member (GMPOI) 600 is preferably a planar member 610 with a parallelogram shape positioned between edges 580 and 580' and handle portion 550 as shown in FIG. 4F. It is preferred that member 610 be angled relative to the body of apparatus 100 such that the forward and rear edges 613 of the member are parallel with the edges 580 and 580' of holder 500. In FIG. 4F lines L3 and L4 illustrate the relative orientation of forward edge 613 and 580 in a preferred embodiment. As can be seen, lines L3 and L4 are parallel to each other, and are not perpendicular to the centerline L1 of holder 100. Member 610 preferably extends above and/or below the gripping surfaces 570 and 570', and more preferably above and/or below the handle portion 550. Member 610 is preferably positioned within 0.5 inches of the forward edges 580 and 580'. Member 610 is preferably perpendicular to the plane formed by edges 580 and 580'. Top and bottom edges 611 and 612 of member 610 are preferably parallel to the centerline of holder 100 as shown by lines L1 and L2 of FIG. 4F.

Preferred embodiments will comprise horizontal position indicators as well as vertical position indicators. In the embodiment shown, GMPOI 600 functions both as a position indicator and an orientation indicator. However, it is contemplated that alternative embodiments may utilize separate and/or additional indicators.

Vertical indication indicator 700 comprises a height gauge formed by tooth occlusal surface contacting member 710, and height indication member 720 as shown in FIG. 4G. The distance D1' between members 710 and 720 is preferred to be fixed during formation of holder 100 and to correspond to a desired distance D1 to allow proper vertical positioning of bracket 10 relative to the occlusal plane P1. Members 710 and 720 are preferred to be parallel to each other. It is also preferred that edges 711 and 721 be adapted to fit within bracket's archwire receiving slots (see FIGS. 8 and 9). Surface contacting member 710 is preferred to be substantially longer than surface contacting member 720 to permit member 710 to contact the occlusal surface of a tooth while edge 721 of member 720 is inserted into a bracket's archwire receiving slots.

In preferred embodiments member 720 will comprise a wire 722, possibly in the form of a loop, with edge 721 being a linear portion of wire 722. Forming edge 721 from wire 722 helps prevent inadvertent movement of a bracket when edge 721 is inserted into the bracket's archwire receiving slots, particularly when those slots are angles. With a wire, bracket holder 100 can rotate around edge 721 and have a minimal impact on a bracket during such a rotation. A tool which cannot be rotated around edge 721 that is inserted into an angled archwire receiving slot will itself be in a non-horizontal position, and thus cannot be used to accurately position the bracket because member 710 will be angled upward or downward.

Figure 7:
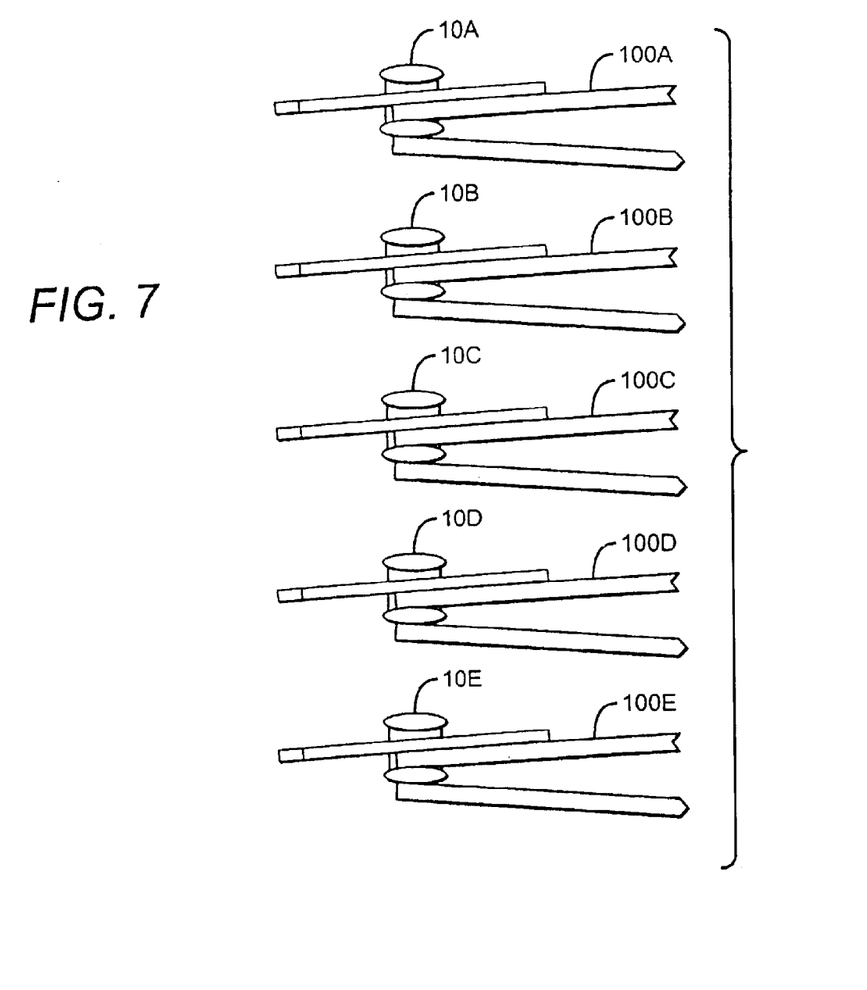
FIG. 7 depicts a set of apparatus where each member of the set is chosen to match the height requirements for a particular tooth of a patient to be treated.

It is preferred that member 710 be parallel to the line L5 formed by points 591 and 592, and be parallel to or coplanar with member 610. Points 591, the point at which members 510 and 510' cross, and 592, the center of the end of the handle portion of the holder, are readily identifiable when looking at apparatus 100. As such, points 591 and 592 provide a convenient means for using apparatus 100 to provide a visual indication of the orientation of members 710 and 610. Consequently, if either member 610 or 710 is inserted into a bracket's archwire receiving slots (as shown in FIGS. 7 and 9), the line extending between points 591 and 592 provides an indication of the orientation of the bracket, and, because of the length of such a line, allows for finer adjustments to the orientation of a bracket than is possible by simply viewing the bracket while it is being gripped by the holder.

FIG. 4H depicts de-biasing portion 551 that serves to decrease the force required to cause holder 100 to open to grip or release a bracket. In the embodiment of FIG. 4, de-biasing portion 551 comprises thinned portions of members 510 and/or 510'. Thinning either or both of members 510 and 510' decreases the force required to separate jaws 520 and 520' without decreasing the vertical rigidity of holder 100. However, alternative means for de-biasing, such as the inclusion of a spring in separation S, are also contemplated.

Apparatus 100 may be used to couple an orthodontic bracket to a tooth by doing one or more of the following: (a) utilizing bracket holder 500 to place a bracket 10 on a tooth 40; (b) while holding bracket 10, positioning and orientating the bracket using/viewing one or more visual indicators to determine the position and orientation of bracket 10; (c) releasing bracket 10; (d) utilizing a height gauge to adjust the vertical position of bracket 10; (e) inserting a portion of the bracket holder 500 into the bracket 10; and (e) rotating the bracket holder 500 while it is inserted into bracket 10 so as to rotate bracket 10. Positioning with the height gauge may be done either before or after rotating holder 500 while it is inserted into bracket 10, but is preferrably done prior to such a rotation step. It is preferred that the portion of the bracket holder 500 inserted into bracket 10's archwire receiving slots be either edge 711 of height gauge 700, or edge 611 or edge 612 of GMPOI 600. In some instances it may be advantageous to use the bracket holder to rotate the bracket without gripping the bracket both before and after using a height gauge to adjust the vertical position of the bracket. Alternative methods may involve placing holder 500 in contact with the top or bottom of bracket 10 rather than inserting into bracket 10 for alignment of bracket 10.

Figure 5:
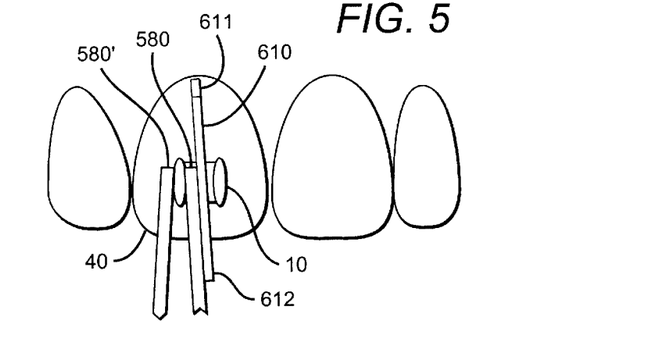
FIG. 5 illustrates a first use of the apparatus of FIG. 4.

Utilizing bracket holder 500 to place bracket 10 on tooth 40 may be accomplished by gripping either both sides of a single stem as shown in FIG. 5, or the outside portions of both stems. In either instance, GMPOI 600 provides a visual indication of both the position and orientation of bracket 10 while the bracket is being gripped. However, as can be seen in FIG. 5, placing GMPOI 600 on the outside surface of member 510' allows GMPOI 600 to be located between stems when a single stem is gripped. In such an instance, GMPOI is aligned with a center line of bracket 10, and can be centered on tooth 40 so as to center bracket 10 on tooth 40 when initially positioning and orientating the bracket.

Once bracket 10 is positioned on tooth 40, GMPOI 600 can be repositioned so that edge 611 or 612 is received by the archwire receiving slots of bracket 10. Utilizing apparatus 100 in this manner provides at least two advantages. The first is that the apparatus acts as a visual indicator of the orientation of bracket 10 as previously discussed. A second is that it makes it easier to rotate bracket 10 by using the length of the apparatus to increase the amount of torque applied to the bracket. Both of these advantages serve to facilitate fine-tuning the orientation of bracket 10. Use of edge 611 or 612 of GMPOI 610 to orient bracket 10 may be optional, may be done either before and/or after the use of height gauge 700, and may be done in place of using edge 711 of height gauge 700 to orientate bracket 10.

For height adjustment, edge 721 of member 720 is inserted into the archwire receiving slots of bracket 10, and the vertical position/height of bracket 10 is adjusted so that member 710 contacts the occlusal surface of tooth 400. In some instances, member 610 may be used as a visual indicator of the orientation of bracket 10 during height adjustment, particularly if member 610 and 720 are parallel or coplanar.

Figure 6:
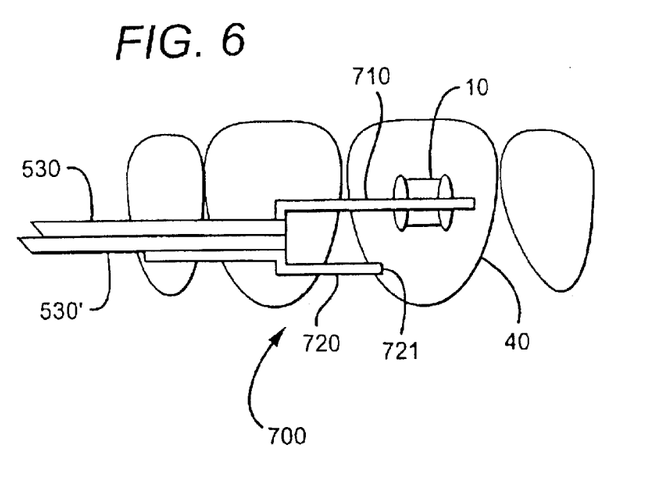
FIG. 6 illustrates a fifth use of the apparatus of FIG. 4.

Referring to FIG. 6, edge 711 of height gauge 700 may be used in a manner similar to that previously described for edge 611 of GMPOI 600. Doing so provides at least the same to advantages as use of edge 611. Similarly, use of edge 711 of height gauge 700 to orient bracket 10 may be optional, may be done either before and/or after the use of GMPOI 600, and may be done in place of using edge 611 of GMPOI 600 to orientate bracket 10.

It is contemplated that it would be advantageous to provide sets of bracket holders where each bracket holder in the set has a height gauge set to a height appropriate for a particular tooth of a patent to be treated using the set. Use of such a pre-loaded set minimizes the amount of time required to mount a complete set of brackets to a patients teeth as it eliminates the time that would be otherwise required to select a bracket holder having an appropriate height. Moreover, if each bracket holder in the set is pre-loaded with a bracket, the time required to properly grasp a bracket is also eliminated. As such, a major portion of the time involved in bracket mounting can be accomplished prior to a patient's arrival, and may be done by a dental assistant following a prescription rather than by the dentist during bracket installation. FIG. 7 illustrates such a preloaded set of bracket holders 100A–100E pre-loaded with brackets 10A–10E. It is contemplated that preferred sets may comprise 20–24 holders, one for each of 20–24 brackets to be positioned. It is also contemplated that the brackets and holders of such a set may be arranged in an order related to the order in which the brackets are to be installed, or an order related to the relative positioning of the patients teeth so as to facilitate identification of the appropriate holder to use for each tooth.

It is contemplated that one method for using such a set for coupling a plurality of orthodontic brackets to a plurality of teeth would include providing a plurality of bracket holders, each holder having a grasping member adapted to receive and hold a bracket; providing a plurality of brackets; and, prior to coupling any one of the brackets to a tooth, causing each bracket holder to receive and hold a bracket. Such a method would preferably also include, prior to coupling any one of the brackets to a tooth, arranging the bracket holders in an order at least partially dependent on the order in which the brackets are to be installed, or at least partially dependent on the relative positions of the teeth to which the brackets are to be coupled.

Each patent or other publication referenced above is incorporated herein by reference in its entirety.

Thus, specific embodiments and applications of holding, positioning, and alignment apparatus have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An apparatus comprising:
   a handle;
   a pair of opposed gripping members, each member comprising a gripping surface, each gripping surface comprising a forward edge;
   a gripping member position and orientation indicator positioned between the handle and the forward edges, wherein the position and orientation indicator does not extend beyond the forward edges of the gripping surfaces, and the indicator extends at an angle above and below the handle.

2. The apparatus of claim 1 wherein the gripping member position and orientation indicator is a planar, non-rectangular parallelogram.

3. The apparatus of claim 1 wherein the gripping member position and orientation indicator is positioned within 0.5 inches from the forward edges.

4. An apparatus comprising:
   a handle;
   a pair of opposed gripping members, each member comprising a gripping surface, each gripping surface comprising a forward edge;
   a gripping member position and orientation indicator positioned between the handle and the forward edges, wherein the position and orientation indicator does not extend beyond the forward edges of the gripping surfaces;
   wherein the gripping edges are coplanor, and the gripping member position and orientation indicator is an elongated planar member the plane of which is perpendicular to the plane of the gripping edges and substantially parallel to the gripping surfaces.

5. An apparatus comprising:
   a handle;
   a pair of opposed gripping members, each member comprising a gripping surface, each gripping surface comprising a forward edge;
   a gripping member position and orientation indicator positioned between the handle and the forward edges, wherein the position and orientation indicator does not extend beyond the forward edges of the gripping surfaces;
   wherein the apparatus comprises a height gauge positioned on an end of the apparatus that does not comprise the pair of gripping members.

6. An apparatus comprising a handle; a pair of opposed gripping members, each member comprising a gripping surface, each gripping surface comprising a forward edge; a gripping member position and orientation indicator positioned between the handle and the forward edges; and a height gauge wherein the height gauge comprises first and second parallel planar members separated by a fixed distance and extending outward from the apparatus with the first parallel planar member being substantially longer than the second parallel planar member, the shorter planar member comprising a wire loop.

7. The apparatus of claim 6 wherein the gripping edges are coplanor, and the gripping member position and orientation indicator is an elongated planar member the plane of which is perpendicular to the plane of the gripping edges, and is parallel to or coplanar with the planar members of the height gauge.

8. A set of orthodontic bracket holders wherein:
   each bracket holder comprises a handle, a pair of opposed gripping members, each member comprising a gripping surface, each gripping surface comprising a forward edge, and a gripping member position and orientation indicator positioned between the handle and the forward edges, wherein the position and orientation indicator does not extend beyond the forward edges of the gripping surfaces;
   each bracket holder of the set comprise a height gauge that corresponds to a prescribed bracket height for a particular tooth of a particular patient, wherein the prescribed heights of at least two holders of the set differ.

9. A method of coupling an orthodontic bracket to a tooth comprising:
   providing a bracket holder;
   utilizing the bracket holder to place a bracket on a tooth;

inserting a portion of a height gauge of the bracket holder into the bracket; and rotating the bracket holder so as to rotate the height gauge inserted into the bracket and thus rotate the bracket.

10. A method of coupling an orthodontic bracket to a tooth comprising:

providing a bracket holder;

utilizing the bracket holder to place a bracket on a tooth;

inserting a portion of a gripping member position and orientation indicator of the bracket holder into the bracket; and rotating the bracket holder so as to rotate the indicator inserted into the bracket and thus rotate the bracket.

11. A method of coupling an orthodontic bracket to a tooth comprising:

providing a bracket holder comprising a gripping member position and orientation indicator;

utilizing the bracket holder to grip a bracket and to place the bracket on a tooth; and while viewing the position and orientation of the gripping member position and orientation indicator relative to the tooth on which the bracket is being mounted, rotating and/or moving the bracket holder so as to set the orientation and position of the bracket.

12. The method of claim 11 further comprising:

subsequently causing the bracket holder to release the bracket;

inserting a portion of the bracket holder into the bracket; and rotating the bracket holder so as to rotate the bracket.

13. The method of claim 12 wherein the portion of the bracket holder inserted into the bracket is part of a height gauge.

14. The method of claim 13 wherein the portion of the bracket holder inserted into the bracket is part of the gripping member position and orientation indicator.

* * * * *